United States Patent
Saad

(10) Patent No.: US 7,201,271 B1
(45) Date of Patent: Apr. 10, 2007

(54) ORAL CARE DEVICE PORTABLE APPARATUS WITH SANITIZING TOWELETTES

(76) Inventor: Jody L. Saad, 1631 Matthew Dr., Fairfield, CA (US) 94533

( * ) Notice: Subject to any disclaimer, the term of this patent is extended or adjusted under 35 U.S.C. 154(b) by 149 days.

(21) Appl. No.: 10/965,097

(22) Filed: Oct. 15, 2004

(51) Int. Cl.
- *A61B 19/02* (2006.01)
- *B65D 1/24* (2006.01)
- *B65D 43/14* (2006.01)
- *B65D 71/00* (2006.01)

(52) U.S. Cl. ............... 206/63.5; 132/315; 206/233; 206/494; 220/522

(58) Field of Classification Search ............... 206/63.5, 206/229, 233, 369, 494, 581; 220/522; 132/314–315
See application file for complete search history.

(56) References Cited

U.S. PATENT DOCUMENTS

| | | | |
|---|---|---|---|
| 2,443,988 A * | 6/1948 | Morse | 220/522 |
| RE35,034 E * | 9/1995 | Albert | 206/63.5 |
| 5,924,562 A | 7/1999 | Barth | |
| 6,164,442 A * | 12/2000 | Stravitz | 220/522 |
| D443,981 S | 6/2001 | DiVincenzo | |
| 6,257,888 B1 | 7/2001 | Barham | |
| 6,305,591 B1 | 10/2001 | Jones | |
| 6,417,761 B1 | 7/2002 | Elliot | |
| 2003/0168357 A1* | 9/2003 | Campbell et al. | 206/63.5 |

* cited by examiner

*Primary Examiner*—Bryon P. Gehman

(57) ABSTRACT

A storage case includes a housing including a base section and a top section pivotally connected thereto. The base section has a substantially planar bottom surface for receiving an oral care device thereon and further has an outer wall integral with the base section and extending upwardly therefrom. The top section includes a compartment including a door pivotally connected thereto. Such a compartment is spaced from the bottom surface when the housing is adapted to a closed position. A plurality of sanitizing towelettes are stored within the compartment and are selectively removable therefrom. Such towelettes are impregnated with predetermined artificial flavors for providing a pleasant taste after the oral care device is wiped between uses thereof.

1 Claim, 2 Drawing Sheets

ORAL CARE DEVICE PORTABLE APPARATUS WITH SANITIZING TOWELETTES

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to a storage case and, more particularly, to a storage case for hygienic articles.

2. Prior Art

An orthodontic retainer is a device used for straightening teeth. In order for orthodontic retainers to perform their intended function, they must be consistently worn in the mouth until the teeth are correctly positioned and preferably, until the tooth root system becomes firm within the supporting bone structure. While children may remove the retainer for eating or brushing teeth, it is advantageous that the retainer be replaced within the mouth as soon as is practicable thereafter. Accordingly, for sanitary purposes, most retainers are dispensed with a case for storing the fixture while it is out of the mouth.

People who have children with orthodontic retainers recognize the problem of enforcing consistent use of the retainer, especially when the retainer becomes dirty and odorous from continuous wear. Children, and adults alike, may use the case for the temporary storage of their retainer during activities requiring removal from the mouth but frequently forget to replace the retainer within the mouth as instructed when such activity is terminated or choose not to do so because the retainer appears unsanitary.

Accordingly, a need remains for a storage case for hygienic articles in order to overcome the above-noted shortcomings. The present invention satisfies such a need by providing a hygienic retainer case that is convenient to use, effective, cost-effective, and provides an increased level of sanitation, thus improving patient care. Such a retainer case effectively stores the retainer during periods of non-use while conveniently allowing a user to clean same before resuming wear after storage. This increases the frequency of wearing a retainer and results in more expedient and improved orthodontic results.

BRIEF SUMMARY OF THE INVENTION

In view of the foregoing background, it is therefore an object of the present invention to provide a storage case for hygienic articles. These and other objects, features, and advantages of the invention are provided by a portable apparatus for shielding and transporting oral care devices.

The apparatus includes a housing including a base section and a top section pivotally connected thereto and movable between open and closed positions along a selected arcuate path. Such a housing may be formed from non-corrosive material and is shaped generally like a retainer employed in the dental industry. The base section has a substantially planar bottom surface for receiving an oral care device thereon and further has a unitary outer wall integral with the base section and extending upwardly therefrom along a substantially vertical plane. The housing preferably further includes a latch attached to a selected portion of the top and base sections so that a user can effectively maintain the housing at a closed position during non-operating conditions.

The top section includes a compartment including a door pivotally connected thereto such that the compartment can be isolated from the base section when the housing is adapted to a closed position. The base section preferably defines a cavity having a greater volume than a volume of the compartment. Such a compartment is defined medially of the top section and spaced from the bottom surface when the housing is adapted to a closed position. The compartment door may be formed from transparent material such that a user can conveniently and readily identify a remaining quantity of towelettes disposed within the compartment without having to pivot the door to an open position. Such a compartment door preferably has a pivot axis extending substantially parallel to a pivot axis of the housing such that the top section and the door can be pivoted along a uniform arcuate plane.

A plurality of sanitizing towelettes are stored within the compartment and are selectively removable therefrom for conveniently wiping and cleansing the oral care device stored in the housing. Such towelettes are impregnated with predetermined artificial flavors for advantageously providing a pleasant taste after the oral care device is wiped between uses thereof.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
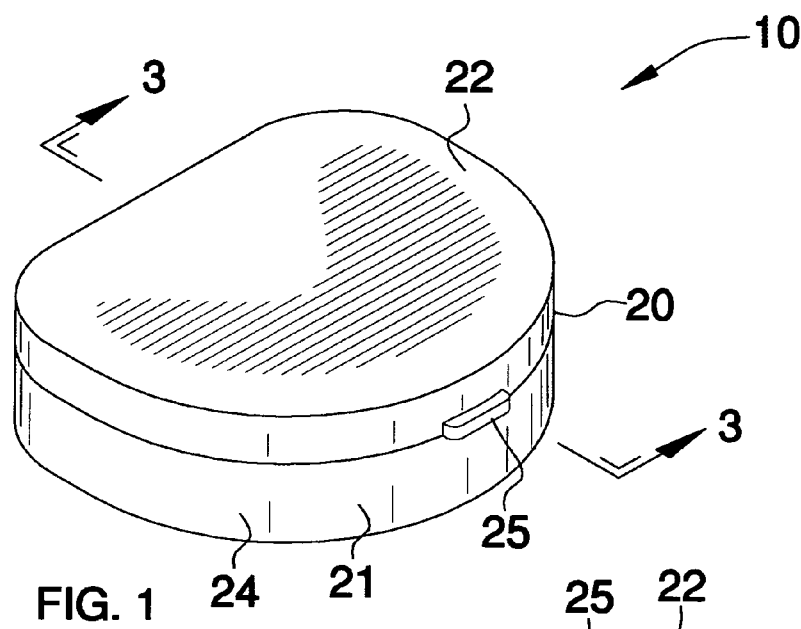
FIG. 1 is a perspective view showing a storage case for hygienic articles, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The apparatus of this invention is referred to generally in FIGS. 1–4 by the reference numeral 10 and is intended to provide a storage case for hygienic articles. It should be understood that the apparatus 10 may be used to store many different types of hygienic devices such as mouth guards and bite plates and should not be limited to only orthodontic retainers.

Referring initially to FIG. 1, the apparatus 10 includes a housing 20 including a base section 21 and a top section 22 pivotally connected thereto and movable between open and closed positions along a selected arcuate path. Such a housing 20 may be formed from non-corrosive material and is shaped generally like a retainer employed in the dental industry. The base section 21 has a substantially planar bottom surface 23 for receiving an oral care device 30 thereon and further has a unitary outer wall 24 integral with the base section and extending upwardly therefrom along a substantially vertical plane. The housing 20 further includes a latch 25 attached to a selected portion of the top 22 and base 21 sections so that a user can effectively maintain the housing 20 at a closed position during non-operating conditions. This feature advantageously prevents the housing 20 from opening and having the retainer 30 fall out only to be lost. Such retainers 30 are very expensive to replace when lost.

Figure 2:
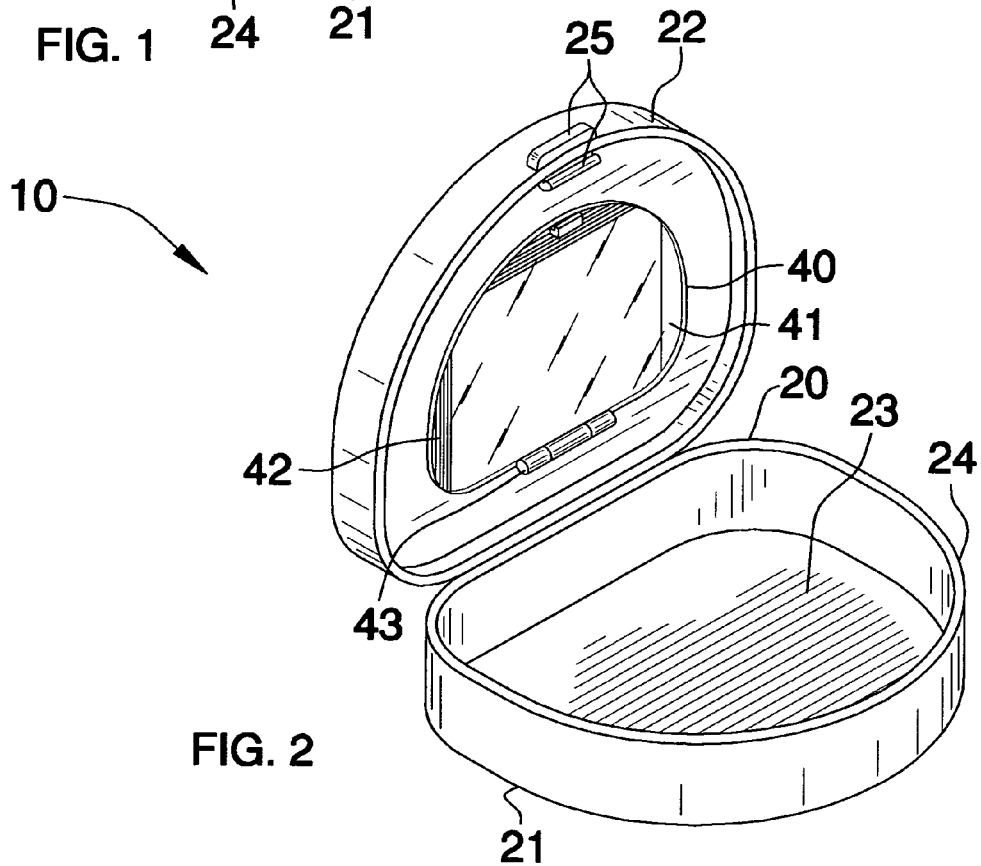
FIG. 2 is perspective view of the apparatus shown in FIG. 1, showing the base and top sections pivotally disconnected.
Figure 3:
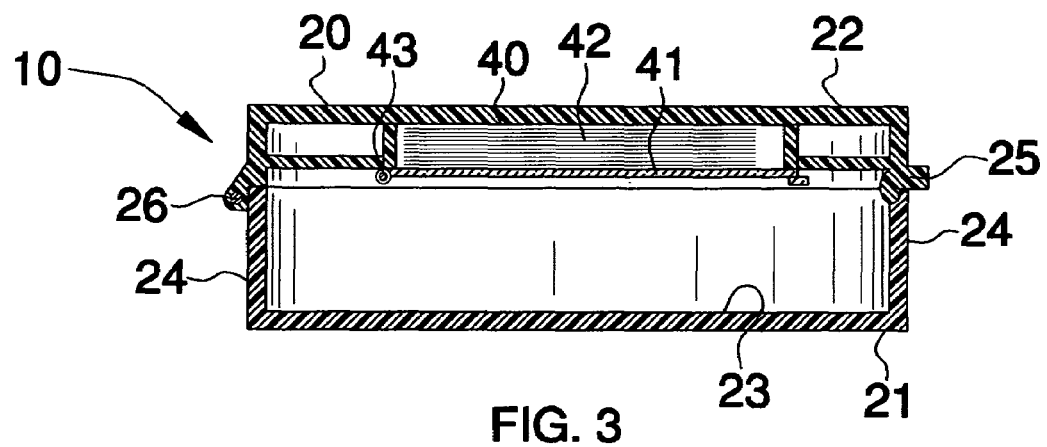
FIG. 3 is a cross-sectional view of the apparatus shown in FIG. 1, taken along line 3—3 showing the top section compartment.
Figure 4:
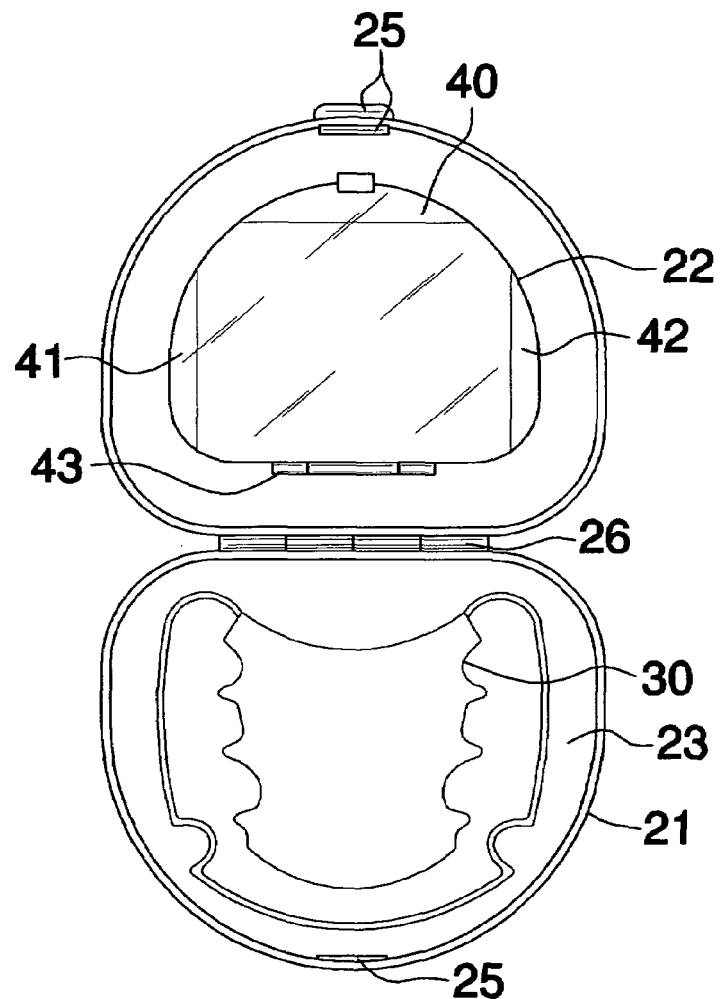
FIG. 4 is a top plan view of the apparatus shown in FIG. 2, showing a retainer and sanitizing towelettes housed therein.

Referring to FIGS. 2, 3 and 4, the top section 22 includes a compartment 40 including a door 41 pivotally connected thereto such that the compartment 40 can be isolated from the base section 21 when the housing 20 is adapted to a closed position. The base section 21 defines a cavity having a greater volume than a volume of the compartment 40. Such a compartment 40 is defined medially of the top section 22 and spaced from the bottom surface 23 when the housing 20 is adapted to a closed position, as best shown in FIG. 3. The compartment door 41 is formed from transparent material such that a user can conveniently and readily identify a remaining quantity of towelettes 42 (described herein below) disposed within the compartment 40 without having to pivot the door 41 to an open position. The fewer times the door 41 is opened the longer the towelettes 42 will retain the impregnated artificial flavors. Such a compartment door 41 has a pivot axis 43 extending substantially parallel to a pivot axis 26 of the housing 20 such that the top section 22 and the door 41 can be pivoted along a uniform arcuate plane.

Still referring to FIGS. 2, 3 and 4, a plurality of sanitizing towelettes 42 are stored within the compartment 40 and are selectively removable therefrom for conveniently wiping and cleansing the oral care device 30 stored in the housing 20. Such towelettes 42 are impregnated with predetermined artificial flavors for advantageously providing a pleasant taste after the oral care device 30 is wiped between uses thereof. The artificial flavors will make the oral care device 30 more appealing to wear and the towelettes will advantageously remove any dried mucus and odor causing bacteria. Due to these features an individual will more readily and frequently wear their oral care device 30 thus increasing the orthodontic benefits associated with the device 10.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A portable apparatus for shielding and transporting an oral care device, said apparatus comprising:

a housing including a base section and a top section pivotally connected thereto and movable between open and closed positions along a selected arcuate path, said base section having a substantially planar bottom surface for receiving an oral care device thereon and further having a unitary outer wall integral with said base section and extending upwardly therefrom along a substantially vertical plane, said top section comprising a compartment including a door pivotally connected thereto such that said compartment can be isolated from said base section when said housing is moved to a closed position, said compartment being defined medially of said top section and spaced from said bottom surface when said housing is moved to said closed position; and a plurality of sanitizing towelettes stored within said compartment and being selectively removable therefrom for wiping and cleansing the oral care device when stored in said housing, said towelettes being impregnated with predetermined artificial flavors for providing a pleasant taste after the oral care device is wiped between uses thereof;

wherein said housing further comprises a latch attached to a selected portion of said top and base sections so that a user can effectively maintain said housing at said closed position;

wherein said compartment door is formed from transparent material such that a user can readily identify a remaining quantity of said towelettes disposed within said compartment without having to pivot said door to an open position;

wherein said compartment door has a pivot axis extending substantially parallel to a pivot axis of said housing such that said top section and said door can be pivoted along a uniform arcuate plane, said pivot axis of said compartment door being disposed along a bottom edge of said compartment door;

wherein said base section defines a cavity having a greater volume than a volume of said compartment;

wherein said housing is formed from non-corrosive material and is shaped generally like its oral care device;

wherein said compartment door has an outer perimeter spaced inwardly from the outer perimeter said top section such that said compartment door detaches and separates from said top section when said compartment door is moved to said open position;

wherein said compartment door is openable downwardly into a cavity of said base section;

wherein said compartment door and said top section each have solid and continuous surfaces.

* * * * *